(12) United States Patent
Hedberg et al.

(10) Patent No.: US 6,944,500 B1
(45) Date of Patent: Sep. 13, 2005

(54) METHOD AND CIRCUIT FOR MONITORING AN OSCILLATOR IN A MEDICAL IMPLANT

(75) Inventors: Sven-Erik Hedberg, Kungsängen (SE); Jonas Andersson, Johanneshov (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 10/009,469

(22) PCT Filed: May 22, 2000

(86) PCT No.: PCT/SE00/01025

§ 371 (c)(1),
(2), (4) Date: May 24, 2002

(87) PCT Pub. No.: WO00/74776

PCT Pub. Date: Dec. 14, 2000

(30) Foreign Application Priority Data

Jun. 3, 1999 (SE) .................................. 9902058

(51) Int. Cl.[7] .............................................. A61N 1/08
(52) U.S. Cl. ........................... 607/27; 600/509; 607/25
(58) Field of Search ................................. 607/27, 2, 62, 607/17–20, 25; 600/509, 521, 516, 528

(56) References Cited

U.S. PATENT DOCUMENTS

| 4,416,282 A | * | 11/1983 | Saulson et al. ................. 607/9 |
| 4,590,941 A | | 5/1986 | Saulson et al. |

FOREIGN PATENT DOCUMENTS

| DE | OS 25 39 592 | 3/1977 |
| GB | 1 599 231 | 9/1981 |

* cited by examiner

*Primary Examiner*—Kennedy Schaetzle
(74) *Attorney, Agent, or Firm*—Schiff Hardin LLP

(57) ABSTRACT

In a method and circuit for monitoring an oscillator in a medical implant, a physiological parameter is obtained from a subject in whom the medical implant is implanted and an electric signal containing a time component, is generated based on the physiological parameter. The functioning of the oscillator is monitored using this electric signal to identify if the functioning of the oscillator deviates from a specified functioning of the oscillator.

26 Claims, 4 Drawing Sheets

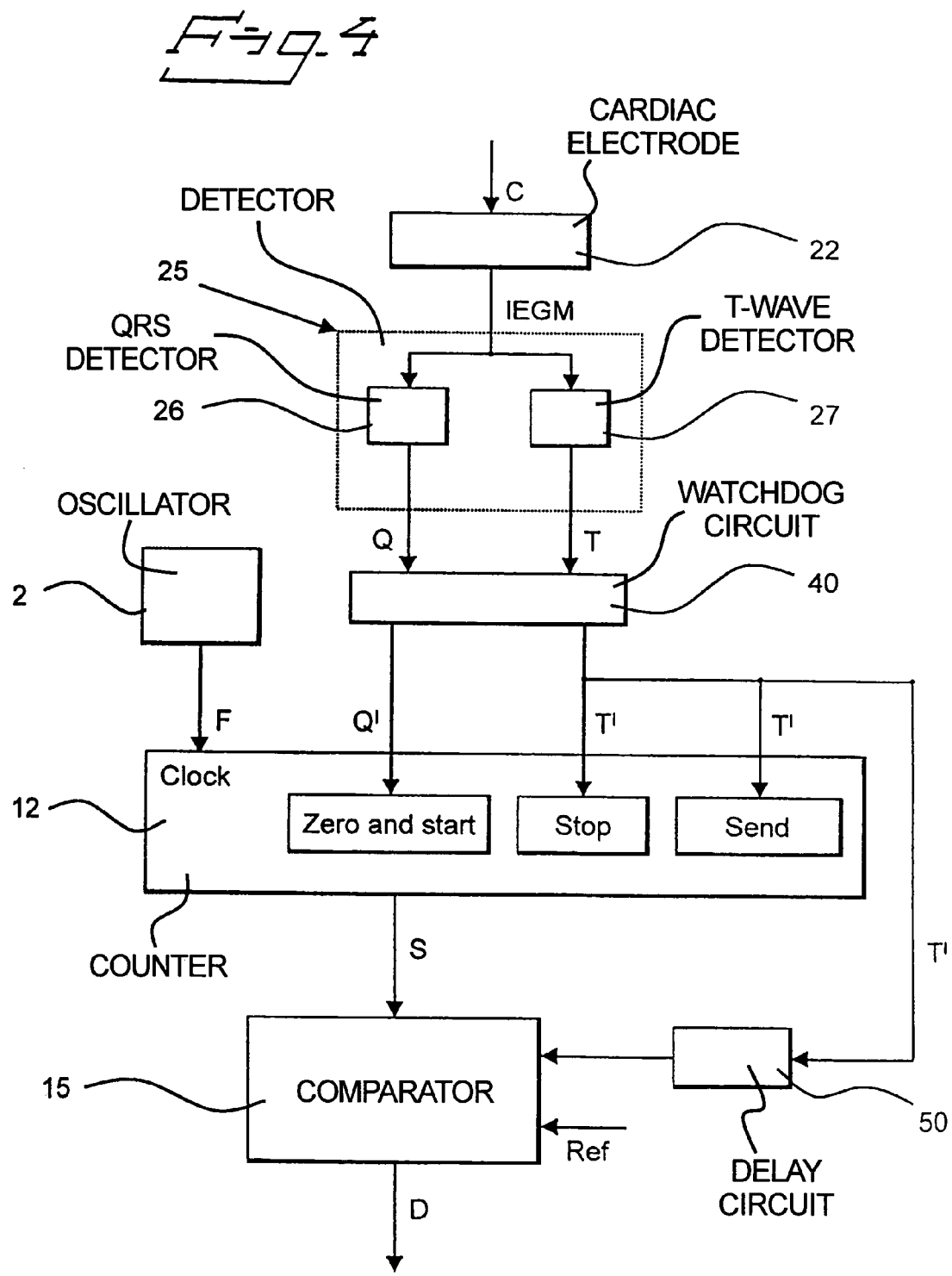

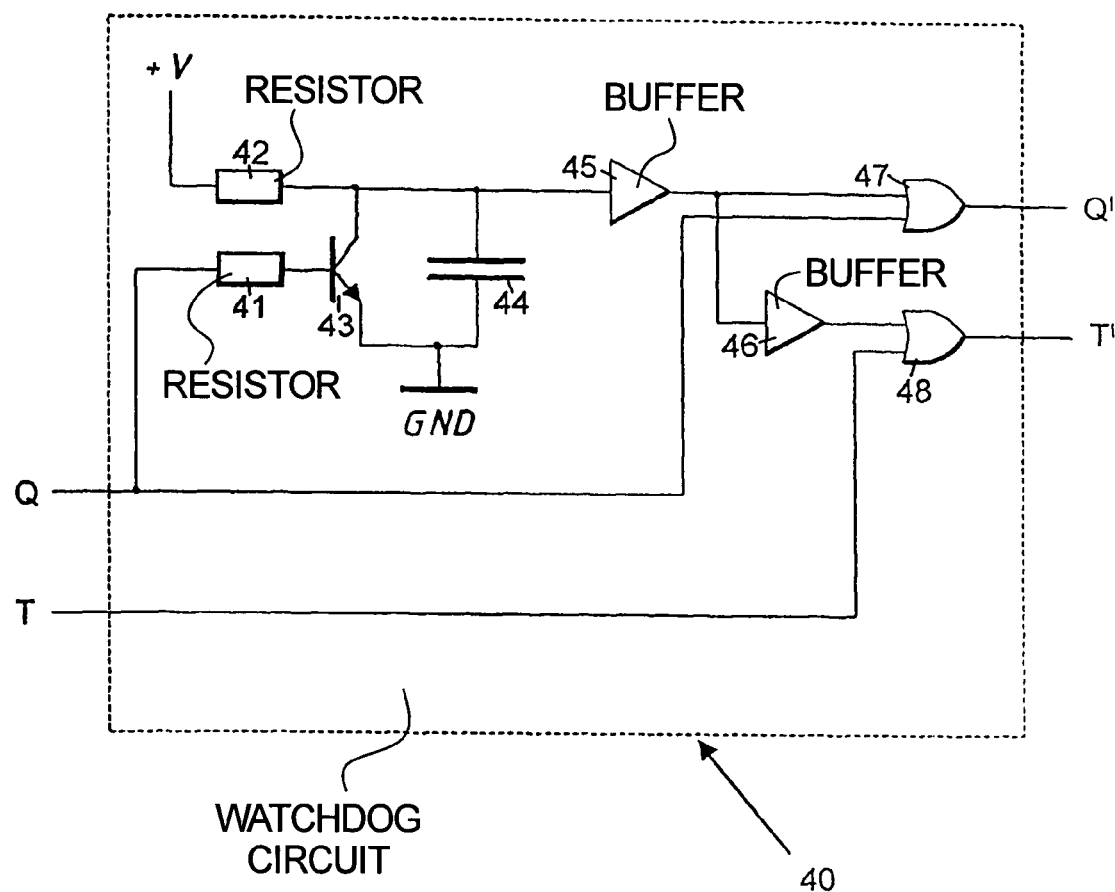

METHOD AND CIRCUIT FOR MONITORING AN OSCILLATOR IN A MEDICAL IMPLANT

BACKGROUND OF THE INVENTION

1. Field of the Invention

The present invention relates generally to the field of medical implants. More specifically, the present invention relates to a medical implant of the type having an oscillator monitoring circuit for monitoring the functioning of an oscillator in the medical implant, and a method for monitoring the functioning of an oscillator in a medical implant, such as a heart stimulator.

2. Description of the Prior Art

For modern electronic circuits, it is generally essential to provide an accurate clocking signal in order to synchronize the different electronic functions of the circuit. Generally, a single master timing source, such as an oscillator, is used to produce a periodic signal at a fixed frequency. An accurate clock signal is imperative for a proper functioning of the electronic circuit. If the frequency of the periodic signal deviates from its predetermined frequency, the circuit will not function in the intended manner.

Within the field of medical implants, i.e. heart stimulators, the master timing source is generally an oscillator. Heart stimulators are life supporting, therapeutic medical devices that are surgically implanted and remain within a person's body for years. Thus, a need exists for monitoring and checking the master oscillator of the heart stimulator to determine if the frequency of the oscillator periodic signals deviates from its predetermined clock frequency and to handle such a deviation if it occurs.

U.S. Pat. No. 4,590,941 discloses a cardiac pacer having stimulating logic for producing an output stimulating signal, the stimulating logic including a crystal oscillator and a digital circuit serving as the pacing logic of the pacer. The pacer further has a continuously operating RC oscillator and a frequency checking circuit. The RC oscillator is an emergency oscillator continuously producing an output at a predetermined acceptable frequency and a predetermined pulse width. The crystal frequency is tested by the frequency checking circuit using the output of the RC oscillator. The pacer further has a gating means for substituting the output of the RC oscillator for the output of the stimulating logic upon detection of failure of the crystal oscillator.

Hence, the reference parameter used for continuously testing the frequency of the crystal oscillator is the output frequency of the RC oscillator. This requires a continuous operation of the RC oscillator. Furthermore, the frequency checking circuit requires a reliable output from the RC oscillator in order to provide a safe and accurate result. Otherwise, the frequency of the crystal oscillator could be considered to deviate from the correct frequency when, in fact, it is the frequency of the RC oscillator that deviates from the predetermined frequency.

It is an object of the present invention to provide a method, and a medical implant using the method, for detecting with improved reliability a frequency deviation of the output frequency of an oscillator in a medical implant.

The above object is achieved in accordance with the principles of the present invention in a method and circuit for monitoring an oscillator in a medical implant wherein at least one physiological parameter, having a time component, is obtained from a subject in whom the medical implant is implanted, and wherein an electrical signal is generated that is related to the time component, and wherein this electrical signal is used as an indicator of a deviation of the functioning of the oscillator from an intended or specified functioning of the oscillator.

The invention is based on using a physiological parameter emanating from the human body for monitoring the status of the output frequency of a timing circuit in a medical implant. Hence, deviations in the output frequency of the timing circuit are detected by using the physiological parameter as a reference. Preferably, the timing circuit is an oscillator.

By using a physiological parameter for detecting a deviation in the output frequency of an oscillator, use is made of a parameter that is always present, i.e. the physiological parameter can be used for detecting a frequency deviation regardless of whether there is a fault in the electronic circuitry or not. This might not always be the case when a parameter obtained from within the electronic circuitry is used for the deviation detection. In fact, a deviation in the output frequency of a main oscillator in an electronic circuit, can cause resulting effects in the electronic circuitry making components within the circuitry unsuitable, or unusable, for providing a reference parameter for the monitoring.

Furthermore, the problem described in relation to prior art regarding the risk of misinterpreting the result, i.e. the output frequency one oscillator being considered to deviate when the deviation occurs in the output frequency of the other oscillator, is eliminated according to the present invention. This is due to the fact that the monitoring of an oscillator does not involve any other oscillator that might be present in the medical implant.

The physiological parameter used for monitoring the output frequency of the oscillator contains a time component. The time component of the physiological parameter is used for monitoring deviation of the frequency from a permitted value or range.

As is known to a person skilled in the art, any physiological parameter varies over time. Therefore, an exact time value can not be obtained from a physiological parameter. However, the typical oscillator used as a main oscillator in a medical implant is a crystal oscillator, which is calibrated before encapsulation by mechanical trimming. It is well known that, if the output frequency of a crystal oscillator deviates from its intended frequency, it deviates drastically, the output frequency for instance changing to zero or multiples of the intended frequency. Thus, a physiological parameter can be used for monitoring the status of an oscillator, even though the parameter varies slightly over time.

DESCRIPTION OF THE DRAWINGS

FIG. 4 is a block diagram of a specific embodiment of the present invention.

FIG. 5 is a block diagram of a watch dog circuit according to the embodiment shown in FIG. 4.

DESCRIPTION OF THE PREFERRED EMBODIMENTS

Figure 1:
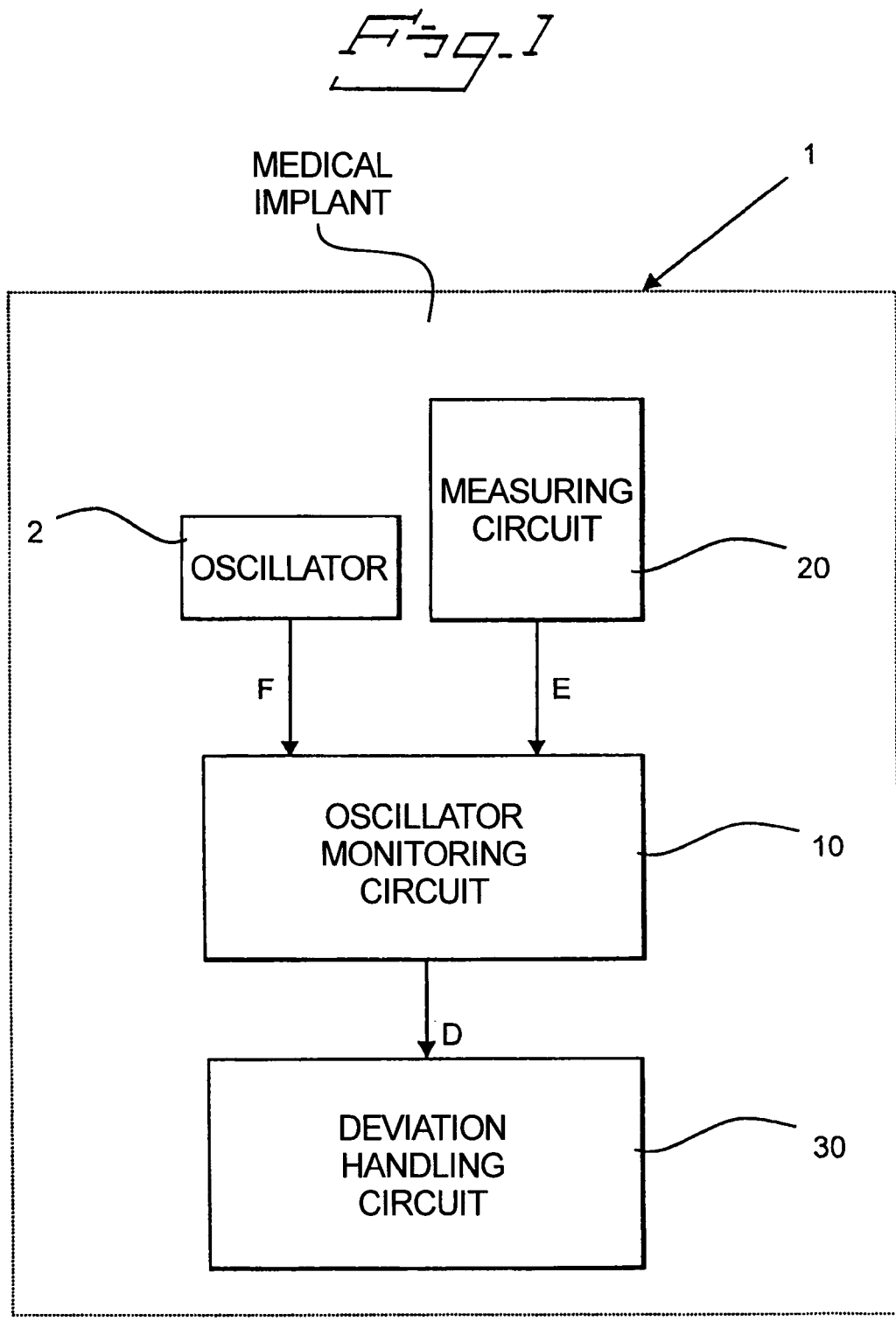
FIG. 1 is a block diagram of a medical implant having an oscillator monitoring circuit according to the present invention.

FIG. 1 is a block diagram of a medical implant 1 having an oscillator 2, an oscillator monitoring circuit 10, a measuring circuit 20 and a deviation handling circuit 30. As is apparent to the person skilled in the art, a medical implant, i.e. a heart stimulator, contains and is connected to a number of additional elements that are essential for the in tended function of the implant, e.g. a pulse generator, telemetry means, etc. However, the functions of these elements are well known within the art and the illustration and description thereof are therefore omitted. Thus, only parts of the medical implant directly related to the present invention are illustrated and described herein.

Figure 2:
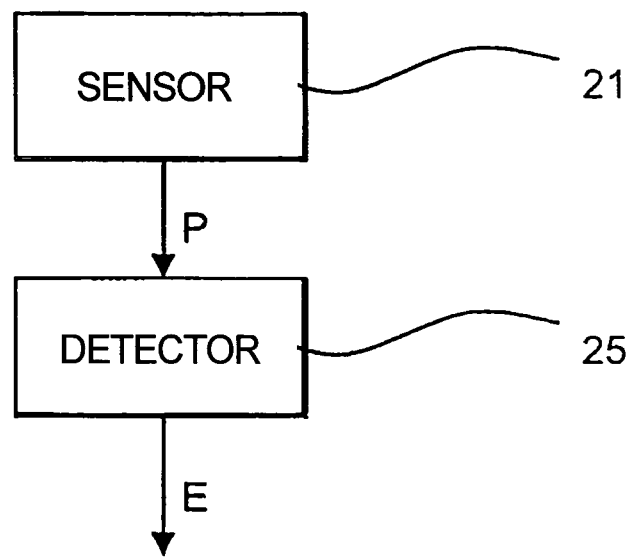
FIG. 2 is a block diagram of the measuring circuit shown in FIG. 1.

As illustrated in FIG. 2, the measuring circuit 20 preferably has a sensor 21, for sensing, or recording, a chosen physiological parameter P, and a detector 25 for detecting characteristics of the chosen physiological parameter P. The sensor type can be chosen among several alternatives and is dependent on the chosen physiological parameter P. The sensor 21 is connected to the detector 25, but is not necessarily contained within the medical implant 1, contrary to what is illustrated in FIG. 1. According to embodiments of the invention, the sensor 21 is situated externally of the medical implant and is connected to the medical implant via electric leads 20 (not shown).

The detector 25 is arranged for detecting characteristics of the physiological parameter P having the chosen time component, the characteristics being dependent on the type of parameter sensed, and for generating an electric signal E containing or being related to these characteristics. The sensor 21 and the detector 25 do not necessarily have to be separate units, instead they can be formed as a single unit for sensing the physiological parameter P and for generating the electric signal B.

Figure 3:
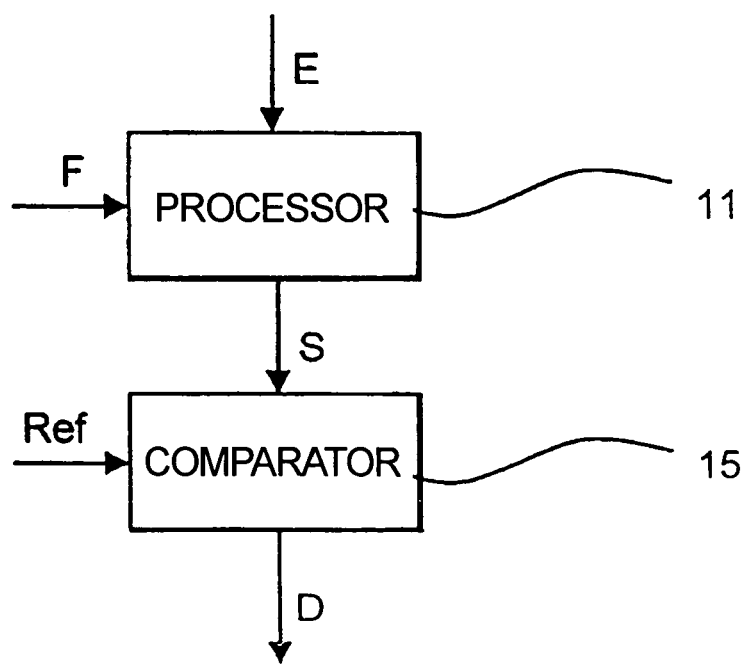
FIG. 3 is a block diagram of the monitoring circuit shown in FIG. 1.

With reference to FIG. 3, the oscillator monitoring circuit 10 preferably has a signal processor 11, receiving the electric signal E and oscillator output frequency F (i.e. the periodic pulses produced by the oscillator), and comparator 15, receiving an oscillator status signal S supplied by the signal processing circuit and a predetermined reference signal Ref, which can be in the form of a value, range, or a template. Preferably, the electric signal B representative of the physiological parameter P is used by the signal processing circuit for generating an oscillator status signal S that reflects the status of the oscillator output frequency F.

The oscillator status signal S can be directly indicative of the output frequency F, e.g. by representing the number of pulses produced by the oscillator 2 during a chosen time interval, or be indirectly indicative of the output frequency F, e.g. by presenting a signal representing a parameter, which in turn is directly dependent on the output frequency F.

The oscillator status signal S is supplied to the comparator 15 for comparing the status signal S with a predetermined reference signal Ref. The reference signal used for this comparison could be a value, a range or a template of some sort, depending on the nature of the physiological parameter. As a result of said comparison, a deviation signal D is produced indicating whether the output frequency of the oscillator is within a permitted value or range.

Preferably, the oscillator status signal S is in the form of a value representing the output frequency F of the oscillator, and the reference signal Ref is in the form of two threshold values representing the permitted maximum and minimum frequencies of the oscillator. In such a case, the deviation signal D preferably has two possible values, the output frequency F lies within the permitted range, or the output frequency F is outside the permitted range. According to an alternative embodiment, the oscillator status signal S represents the morphology of a physiological parameter P, e.g. heart sounds, and the comparator 15 compares the oscillator status signal S to a template using neural networks. Several other alternatives regarding the form of the oscillator status signal S and the reference signal Ref are conceivable without departing from the scope of the present invention.

According to preferred embodiments of the present invention, the physiological parameter P used for the monitoring of the status of the oscillator 2 is the electrical signal emitted by active cardiac tissue, which for ease of description hereinafter will be re10 f erred to as the cardiac signal C. The cardiac signal C is typically recorded through cardiac electrodes and the graphic depiction of the signal is normally referred to as an electrocardiogram (ECG). If the electrodes are placed on or within the heart, the graphic depiction is referred to as an intracardiac electrogram (IEGM). The characteristic portions of the ECG or IEGM are very well known and will be referred to without further description in detail.

The time component used for the oscillator monitoring preferably is obtained within a cardiac cycle, particularly within the systolic phase thereof. The physiological parameters could for instance be related to the width of the QRS-complex or to the QT-interval (i.e. related to the ejection phase of the heart). The parameters related to the width of the QRS-complex preferably is derived from the IEGM by means well known in the art. The parameters related to the QT-interval may be derived directly from the IEGM or indirectly by means of pressure measurements in the ventricle, by impedance measurements, by means of heart sounds such as the valve sounds. Corresponding methods are well known in the art. Such comparison is preferably performed repeatedly for achieving a continuous monitoring of the oscillator status using the IEGM or corresponding parameters of the latest heart beat.

With reference to FIGS. 4 and 5, the most preferred embodiment of the present invention will now be described. The cardiac electrical activity (i.e. the cardiac signal C) is sensed through at least one cardiac electrode 22 positioned within the patient's heart. The sensed parameter is supplied, now in the form of an IEGM, to the detector 25, in this case constituting a QRS detector 26 and a T-wave detector 27 that both receives the IEGM. The QRS detector 26 detects the QRS complex, i.e. the R-peak, and the T-wave detector 27 consequently detects the T-wave. The detectors 26, 27 generate a QRS-detector output signal Q and a T-wave detection signal T, respectively, in the form of a short pulse when the respective event is detected.

The chosen time component of the physiological parameter P used for said monitoring is in this case the time period between the QRS complex and the T-wave of the IEGM, this time period hereinafter being referred to as the QT-interval. The QT-interval is relatively easy to measure and use is preferably made of the existing cardiac electrode(s) used for stimulating (and sensing) in the ventricle for sensing the QRS complex and the T-wave. The QT-interval typically varies within the range of 250 to 350 ms and is substantially independent of the output of the main oscillator. There may he some, but very small, correlation since the QT-interval depends upon the stimulation rate. The QT-interval is therefore very useful and is preferred as the physiological parameter used for the monitoring.

Returning to FIG. 4, the electric signal E, being divided into the QRS detection signal Q and a T-wave detection signal T, is supplied via a watch dog circuit 40 to the signal processing 11, the signal processing circuit here being a counter 12. The watch dog circuit 40 is provided between the detector 25 and the counter 12 for handling a specific situation and will he described in detail below with reference to FIG. 5. The function of the counter 12 is as follows. The counter 12 will be reset by a QRS event, i.e. a pulse in the QRS detection signal Q. The pulse will also trigger the counter 12 to start counting received periodic pulses F produced by the main oscillator 2. At the reception of a pulse in the T-wave detection signal T, the counter 12 will stop counting and the counted number of received pulses during the QT-interval will be sent as the oscillator status signal S to the comparator 15.

The QT-interval will then be compared, by the comparator 15, with predefined QT-interval threshold values provided by a reference signal Ref, corresponding to the QT-interval at the maximum and minimum, respectively, permitted main oscillator frequency. The T-wave detection signal T is also provided to the comparing means 15 via a delay circuit 50 for triggering the comparison. The delay circuit 50 ensures that sufficient time has elapsed for the calculation to be completed before the triggering of the comparison. The result of the comparison will he supplied as a deviation signal D indicating whether the output frequency F of the oscillator 2 lies within the permitted range.

With reference to FIG. 5, the function of the watch dog circuit 40 will be described. If no signal for triggering the comparison and providing a deviation signal, i.e. the T-wave detection signal T, is provided to the comparator 15, no comparison would be carried out and the information contained in the deviation signal D would not change to describe the current status, provided that the oscillator status has changed. One attempt to solve this problem could be to perform a comparison after a given time delay without reception of the T-wave detection signal T. However, this would require some sort of timing signal to be provided. If no output pulses are received from the oscillator 2 this would not be indicated in the deviation signal U if no T-wave detection signal C for triggering the comparison is received from the T-wave detector, i.e. if the patient has no intrinsic rate.

In order to solve this potentially serious problem, the watch dog circuit 40 is provided. The watch dog circuit 40 is provided for delivering a pulse after a predetermined time in the absence of a QRS detection signal Q and a T-wave detection signal T. The circuit 40 has a first resistor 41, a second resistor 42, a transistor 43, a capacitor 44, a first buffer circuit 45, a second buffer circuit 46, a first OR-gate 47, and a second OR-gate 48. As is apparent from FIG. 5, when a QRS detection signal Q or a T-wave detection signal T, respectively, are received, these signals are supplied via the respective OR-gates 47, 48 as QRS detection signal $Q'$ and T-wave detection signal $T'$, respectively. The respective detection signals Q, T pass through the watch dog circuit essentially unchanged, even though the output detection signals $Q'$, $T'$ supplied to the comparing means have a difference reference character in the figure.

If there were no QRS detection signal Q, there would be no T-wave signal T. If there is a QRS signal, there will be a T-wave signal. Thus, the situation to be considered is the loss of both the QRS and the T-wave detection signals. The capacitor 44 is connected to ground and will be charged by the voltage supplied via the second resistor 42. The time constant of the circuit is dependent of the second resistor 42 and the capacitor 44. The charging of the capacitor 44 increases the potential of the side connected to the first buffer circuit 45. When the potential reaches a predefined level, the buffer circuit 45 goes high. If a QRS detection signal Q is supplied to the watch dog circuit 40, this will cause the transistor 43 to short-circuit and discharge the capacitor 44 and the potential of the first buffer circuit 45 will drop to zero before the first buffer circuit 45 goes high. However, if no QRS detection signal Q is supplied, a pulse is supplied by the first buffer circuit 45 to the first OR-gate 47 and, via the second buffer circuit 46, to the second OR-gate 48.

Then, the pulse will be supplied in place of the QRS and T-wave detection signals $Q'$, $T'$ to the counter, with a slight delay for the T-wave detection signal $T'$ caused by the second buffer circuit 46, and a low pulse count, corresponding to the delay caused by the second buffer circuit 46, will be sent to the comparator 15 as the status oscillator signal S. The T-wave detection signal $T'$ will also trigger the comparison. Since the value of the status oscillator signal S will not lie within the predefined permitted range, the deviation signal D will indicate that the output frequency F of the oscillator has deviated from the permitted range.

According to another embodiment of the present invention the width of the QRS complex is measured and used for said monitoring. The variation of the QRS width is somewhat greater than that of the QT-interval. Like the QT-interval, this parameter can easily be measured using the cardiac electrode(s) and requires no additional electronic circuitry. Preferably, the number of output pulses from the oscillator to be monitored is counted, preferably using the counter 12 in the signal processing circuit, during the duration of 30 the QRS, and is supplied as an oscillator status signal S.

Another example of using the IEGM for the monitoring is using the paced depolarization integral (PDI). The PDI is a well-known parameter chat denotes the integral of the QRS complex of the IEGM from the base line. The PDJ essentially is constant from beat to beat. Preferably, PDJ is obtained using integrating means comprised in the signal processing circuit. In similarity with the above embodiments, using the PDI requires no additional sensors (e.g. electrodes) or circuitry. The variation of the PDI corresponds with the QRS width, and the obtained value of the PDI is supplied as the electric signal E, as illustrated in FIG. 3. Since the calculated value of the PDI varies in dependence on the output frequency F, the oscillator status signal S is based on the electric signal E, containing the PDI value, and the output frequency F. The integral is calculated by means of the output frequency and the value of the PDI will deviate from the normal value if the frequency deviates from the standard value. If the oscillator status signal S is determined to be outside predetermined threshold values, this will indicate that the oscillator frequency deviates from the permitted range.

Other physiological parameters are envisioned for monitoring the status of the main oscillator 2. According to one alternative embodiment the physiological parameter is the heart sounds or sound waves produced when the heart operates, e.g. sounds associated with valve opening and closing and diastolic filling sounds. As is the case with the characteristics of the ECG or the IEGM, the sound waves correspond to specific events in the cardiac cycle and have a characteristic morphology. Thus, the time information obtained from heart sounds is considered to be as accurate, or vary as little, as the QT-interval.

The morphology may be analyzed in several ways. According to a first example of alternative embodiments of the present invention, the number of pulses output by the oscillator between detected specific events in the sound waves of the cardiac cycle is counted and supplied as an oscillator status signal S for subsequent comparison with threshold values Ref.

There are several ways of detecting heart sounds, including using a microphone or an accelerometer. The advantage of using an accelerometer is that accelerometers are often used in rate responsive heart stimulators for determining the level of physical activity of the patient. Thus, such an accelerometer could also be used for detecting heart sounds, and no additional sensor 10 means would be required. If the heart sounds are detected by a microphone, however, then an additional component that normally is not found in a medical implant or heart stimulator is used. There may also be a problem in detecting the heart sounds as distinctly as is required for determining the time for specific events of the cardiac cycle, due to the interference of the external environment.

According to preferred embodiments of the invention, the medical implant has back-up timing circuit (not shown), preferably an oscillator, for acting as a main timing circuit, or oscillator, when the output frequency of the original main oscillator 2 deviates outside the predefined permitted range. The back-up oscillator is preferably an RC oscillator, or a current controlled oscillator, for the purpose of providing a back-up timing source that is small and light in weight.

As is shown in FIG. 1, the deviation handling circuit 30 is connected to the monitoring circuit 10, preferably to the comparator 15, for handling a deviation in the output frequency F of the main oscillator 2. The handling circuit 30 is activated when the received deviation signal U indicates a deviation, i.e. when the output frequency F deviates outside the permitted range. The handling circuit 30 contains the back-up oscillator (not shown), for producing periodic pulses normally not being used in the operation of the medical implant, and switching circuitry (not shown) connected to the main oscillator and the back-up oscillator for switching between the normal state and a deviation state. The switching between the respective state is performed by disconnecting the main oscillator 2 and by simultaneously connecting the back-up oscillator such that the periodic pulses produced in the back-up oscillator are used in the operation of the medical implant. According to preferred embodiments of the invention, the status of the back-up oscillator is also monitored by the monitoring means of the present invention, in the manner described above. However, since the back-up oscillator is normally not used for the normal function of the medical implant, the monitoring of the back-up oscillator can be per formed regularly but at a substantially lower rate than the monitoring of the main oscillator, which should be performed continuously.

According to an alternative embodiment of the invention, the deviation handling circuit 30 includes an alarm generator for providing an alarm signal when the deviation signal U indicates that the output frequency F of the oscillator 2 deviates outside the permitted range. The alarm signal could be in the form of a signal that can be observed or sensed by the patient, e.g. an acoustic signal, or a signal that is transmitted to an external apparatus using the telemetry functions generally provided in a medical implant. The alarm signal could be provided in combination with the switching to the backup oscillator, or as a separate action, e.g. indicating that the patient should contact his/her physician but that the need for switching to the back-up oscillator has not arisen. A detected deviation in the output frequency of the back-up oscillator, when functioning as such, is preferably handled by the handling circuit 30 activating an alarm signal. Switching to the other oscillator will not be necessary since the back-up oscillator in this case is not involved in the normal operation of the medical implant.

The timing circuits used in the medical implant according to present invention are preferably oscillators, wherein as the main oscillator use is preferably made of a crystal oscillator, due to the superior reliability of crystal oscillators.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical implant comprising:
an oscillator which emits an oscillator output, said oscillator being designed to emit a specified oscillator output;
a measuring arrangement adapted to interact with a living subject to obtain a physiological parameter having a time component, said measuring arrangement generating an electrical signal dependent on said time component; and
an oscillator monitoring circuit connected to said oscillator and to said measuring arrangement, said oscillator monitoring circuit receiving said oscillator output and said electric signal respectively from said oscillator and said measuring arrangement and, using said electric signal, identifying a deviation of said oscillator output from said specified oscillator output and, if said deviation is identified, emitting a deviation signal indicating identification of said deviation.

2. A medical implant as claimed in claim 1 wherein said oscillator monitoring circuit comprises a signal processor for processing said electric signal and said oscillator output to generate an oscillator status signal, and a comparator supplied with said status signal which compares said status signal to a reference signal representing said specified oscillator output, to generate said deviation signal.

3. A medical implant as claimed in claim 2 wherein said measuring arrangement includes a sensor for sensing said physiological parameter.

4. A medical implant as claimed in claim 3 wherein said sensor comprises cardiac electrodes adapted to detect cardiac electrical activity, as said physiological parameter, said cardiac electrodes generating an intracardiac electrogram representing said cardiac electrical activity, said intracardiac electrogram containing said time component.

5. A medical implant as claimed in claim 4 wherein said measuring arrangement comprises a detector connected to said sensor for detecting a QRS complex and a T-wave in said intracardiac electrogram, said detector generating said electric signal, and said electric signal comprising a QRS detection signal and a T-wave detection signal.

6. A medical implant as claimed in claim 5 wherein said oscillator emits periodic pulses as said oscillator output, and wherein said signal processor comprises a counter connected to said detector for receiving said QRS detection signal and said T-wave detection signal therefrom, and connected to said oscillator for receiving said periodic pulses therefrom, said counter counting a number of said periodic pulses received between reception by said counter of said QRS detection signal and reception by said counter of said T-wave detection signal, and emitting said number as said oscillator status signal.

7. A medical implant as claimed in claim 4 wherein said oscillator emits periodic pulses as said oscillator output, and wherein said measuring arrangement comprises a detector connected to said sensor for detecting a QRS complex in said intracardiac electrogram, said detector generating said electric signal, and said electric signal comprising a QRS signal indicating a beginning and an end of said QRS complex, and said signal processor comprising a counter connected to said detector for receiving said QRS signal therefrom, and to said oscillator for receiving said periodic pulses therefrom, said counter counting a number of said periodic pulses received by said counter between said beginning and said end of said QRS complex, and emitting said number as said oscillator status signal.

8. A medical implant as claimed in claim 4 wherein said measuring arrangement comprises a detector connected to said sensor for detecting a QRS complex, said detector generating said electric signal and said electric signal having an amplitude during said QRS complex, and wherein said signal processor includes an integrator connected to said detector for receiving said electric signal therefrom, said integrator integrating said amplitude during said QRS complex to obtain an integration result, and emitting said integration result as said oscillator status signal.

9. A medical implant as claimed in claim 3 wherein said sensor comprises a microphone for detecting periodic heart sounds as said physiological parameter, and for converting said periodic heart sounds into an electric periodic sound signal having said time component, and wherein said measuring arrangement comprises a detector connected to said microphone for detecting a selected characteristic of said electric periodic sound signal, said detector generating said electric signal and said electric signal representing said characteristic, and wherein said signal processor generates said status signal dependent on said characteristic in said electric signal.

10. A medical implant as claimed in claim 2 wherein said comparator compares said oscillator status signal with a reference signal representing a threshold range, and emits said deviation signal if said oscillator status signal is outside of said threshold range.

11. A medical implant as claimed in claim 2 further comprising a deviation handling circuit connected to said oscillator monitoring circuit for receiving said deviation signal therefrom, said deviation handling circuit initiating predetermined remedial action upon receipt of said deviation signal.

12. A medical implant as claimed in claim 11 wherein said oscillator emits periodic pulses as said oscillator output, and wherein said medical implant includes at least one operating component normally supplied with said periodic pulses from said oscillator, and wherein said deviation handling circuit comprises:
   a back-up oscillator which emits periodic pulses, said periodic pulses from said back-up oscillator normally being isolated from said operating component; and
   switching circuitry connected to said oscillator and to said back-up oscillator for, upon said deviation handling circuit receiving said deviation signal, disconnecting said oscillator from said operating component and connecting said back-up oscillator to said operating component so that said operating component receives said periodic pulses from said back-up oscillator.

13. A medical implant as claimed in claim 12 wherein said back-up oscillator is designed to emit a specified back-up oscillator output, including said periodic pulses, and wherein said oscillator monitoring circuit is connected to said back-up oscillator and identifies a further deviation between said back-up oscillator output and said specified back-up oscillator output, and generates a further deviation signal if said further deviation is identified, said further deviation signal being supplied to said deviation handling circuit and said deviation handling circuit initiating further remedial action involving said back-up oscillator upon receipt of said further deviation signal.

14. A medical implant as claimed in claim 12 wherein said back-up oscillator is an RC oscillator.

15. A medical implant as claimed in claim 11 wherein said deviation handling circuit includes an alarm unit which emits an alarm signal upon receipt of said deviation signal.

16. A medical implant as claimed in claim 1 wherein said oscillator is a crystal oscillator.

17. A method for monitoring a functioning of an oscillator in a medical implant, comprising the steps of:
   obtaining at least one physiological parameter from a living subject in whom said medical implant is implanted, said physiological parameter containing a time component; and
   monitoring functioning of an oscillator in said medical implant, and using said physiological parameter for monitoring said functioning of said oscillator.

18. A method as claimed in claim 17 wherein the step of monitoring functioning of said oscillator comprises detecting a deviation in the functioning of said oscillator from a specified functioning of said oscillator; and
   generating a deviation signal if said deviation is identified.

19. A method as claimed in claim 18 wherein the step of obtaining said physiological parameter comprises:
   sensing said physiological parameter with a sensor adapted for interacting with said subject; and
   generating an electrical signal based on said physiological parameter;
   and wherein the step of identifying said deviation comprises:
   processing said electric signal to obtain an oscillator status signal; and
   comparing said oscillator status signal with a reference signal representing said specified functioning of said oscillator.

20. A method as claimed in claim 19 wherein the step of sensing said physiological parameter comprises sensing cardiac electrical activity, and wherein the step of generating an electric signal comprises generating an intracardiac electrogram as said electric signal, said intracardiac electrogram containing said time component.

21. A method as claimed in claim 20 wherein said oscillator emits periodic pulses as an oscillator output, and wherein the step of processing said electric signal comprises:
   detecting a QRS complex in said intracardiac electrogram;
   detecting a T-wave in said intracardiac electrogram;
   counting a number of said periodic pulses emitted by said oscillator between detection of said QRS complex and detection of said T-wave; and
   using said number as said oscillator status symbol.

22. A method as claimed in claim 19 wherein the step of comparing said oscillator status signal with a reference signal comprises comparing said oscillator status signal to two reference signals representing a reference range; and
   generating said deviation signal if said oscillator status signal is outside of said reference range.

23. A method as claimed in claim 18 comprising automatically initiating remedial action in said medical implant to obtain an oscillator output conforming to said specified functioning of said oscillator.

24. A method as claimed in claim 23 wherein the step of initiating remedial action comprises:
   activating a previously non-activated back-up oscillator which generates said specified functioning of said oscillator; and
   disconnecting said oscillator in said medical implant from components in said medical implant in need of said specified functioning of said oscillator, and connecting said back-up oscillator to said components.

25. A method as claimed in claim 24 comprising the steps of:
   monitoring said back-up oscillator and generating a further deviation signal if functioning of said back-up oscillator deviates from said specified functioning of said oscillator; and
   automatically initiating further remedial action if said further deviation signal is generated.

26. A method as claimed in claim 23 wherein the step of automatically initiating remedial action includes generating an alarm signal.

* * * * *